United States Patent [19]

Kühle et al.

[11] 4,162,329
[45] Jul. 24, 1979

[54] COMBATING FUNGI WITH DICARBOXYLIC ACID MONO-ARYLHYDRAZIDES

[75] Inventors: Engelbert Kühle, Bergisch-Gladbach; Erich Klauke, Odenthal; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 879,547

[22] Filed: Feb. 21, 1978

[30] Foreign Application Priority Data

Mar. 22, 1977 [DE] Fed. Rep. of Germany ....... 2712434

[51] Int. Cl.$^2$ ................ A61K 31/175; A61K 31/195; C07C 130/30
[52] U.S. Cl. ................................. 424/319; 562/437; 562/439
[58] Field of Search ................. 562/437, 439; 424/319

[56] References Cited

U.S. PATENT DOCUMENTS

| | | | |
|---|---|---|---|
| 3,157,699 | 11/1964 | Daniels | 562/439 |
| 3,162,680 | 12/1964 | Biel | 562/439 |
| 3,274,232 | 9/1966 | Hinman et al. | 562/439 X |
| 3,288,848 | 11/1966 | Hinman et al. | 562/439 |
| 3,894,083 | 7/1975 | Hofer et al. | 562/439 X |

FOREIGN PATENT DOCUMENTS 1001854 1/1957 Fed. Rep. of Germany.

OTHER PUBLICATIONS

Druey et al., Helvetica Chemica Acta, 37, (1954) pp. 510-520.
Kirchner et al., Journal of Am. Chem. Soc., 81, (1959), pp. 1721-1726.

Primary Examiner—James O. Thomas, Jr.
Assistant Examiner—Vera C. Clarke
Attorney, Agent, or Firm—Sprung, Felfe, Horn, Lynch & Kramer

[57] ABSTRACT

Combating fungi with dicarboxylic acid mono-arylhydrazides of the formula

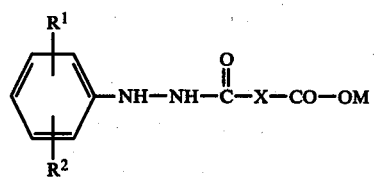

in which
$R^1$ and $R^2$ each independently is hydrogen, halogen, $C_1$-$C_4$ alkyl, $C_1$-$C_4$ alkoxy, $C_1$-$C_4$ alkylmercapto, trihalogenomethyl, trihalogenomethoxy, trihalogenomethylmercapto or nitro,
X is an alkylene, alkenylene, cycloalkylene, cycloalkenylene, cycloalkadienylene or phenylene radical, and
M is hydrogen or one equivalent of a metal, or a salt thereof.

7 Claims, No Drawings

COMBATING FUNGI WITH DICARBOXYLIC ACID MONO-ARYLHYDRAZIDES

The present invention relates to and has for its objects the combating of fungi with dicarboxylic acid mono-arylhydrazides or salts thereof as well as active compositions in the form of mixtures of such compounds with solid and liquid dispersible carrier vehicles, with other and further objects becoming apparent from a study of the within specification and accompanying examples.

It has already been disclosed that certain organic hydrazine compounds can be used as fungicides. For example, quinone-oxime-benzoylhydrazone exhibits an action as a seed dressing (see, for example, DT-AS (German Published Specification) 1,001,854). However, the action is inadequate in the case of seed-borne cereal diseases.

It has been found that the dicarboxylic acid mono-arylhydrazides and their salts of the general formula

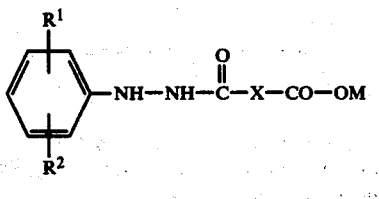

in which
R$^1$ and R$^2$, which may be identical or different, each represent hydrogen, halogen, C$_1$-C$_4$ alkyl, C$_1$-C$_4$ alkoxy, C$_1$-C$_4$ alkylmercapto, trihalogenomethyl, trihalogenomethoxy, trihalogenomethylmercapto or nitro, X represents an alkane, alkene, cycloalkane, cycloalkene or cycloalkadiene grouping or phenylene and M represents hydrogen or one equivalent of a metal, exhibit powerful fungicidal properties.

Preferably, R$^1$ and R$^2$, which may be identical or different, each represent hydrogen, chlorine, methyl, methoxy, methylmercapto, trifluoromethyl, trifluoromethoxy, trifluoromethylmercapto or nitro, and X denotes a straight-chain or branched alkane or alkene grouping with 2 to 4 carbon atoms, a cycloalkane, cycloalkene or cycloalkadiene group with 4 to 7 carbon atoms or a phenylene radical. M is preferably hydrogen, an alkali or alkaline earth metal or an ammonium radical, especially sodium or potassium.

Surprisingly, the dicarboxylic acid mono-arylhydrazides and their salts of the formula (I) exhibit a substantially greater fungicidal action in the case of seed-borne cereal diseases than the above-mentioned compounds known from the prior art. The active compounds which can be used according to the invention thus represent an enrichment of the art.

Some of the dicarboxylic acid mono-arylhydrazides to be used according to the invention are already known (see Helv. Chim. Acta 37, 510 (1954); and J. Am. Chem. Soc. 81, 1721 (1959)).

Many of the compounds according to the invention have not been described in the literature but can be prepared in accordance with known processes by reacting an arylhydrazine of the general formula

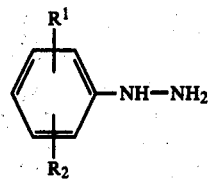

in which
R$^1$ and R$^2$ have the above-mentioned meanings, with a dicarboxylic acid anhydride of the general formula

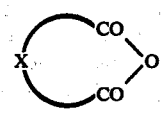

in which X has the above-mentioned meaning, in the presence of a diluent, such as an ether, for example diethyl ether or dioxane, a hydrocarbon, for example toluene or xylene, or a chlorinated hydrocarbon, such as chloroform or chlorobenzene, at temperatures between 0° to 100° C., preferably at from 20° to 50° C., to give a compound of the general formula (I).

To convert the compound (I) into a suitable salt, an alkali metal hydroxide or alkaline earth metal hydroxide is added to neutralize it, and, where appropriate, the compound may be precipitated with a heavy metal salt.

Examples of suitable arylhydrazines of the formula (II) are phenyl-, 2-chlorophenyl-, 3,4-dichlorophenyl-, 3-chloro-4-methylphenyl-, 4-methoxyphenyl-, 3-chloro-4-methylmercaptophenyl, 3-trifluoromethylphenyl-, 3-chloro-4-trifluoromethylphenyl-, 3-chloro-4-trifluoromethoxyphenyl-, 4-methyl-3-trifluoromethylphenyl-, 3-chloro-4-difluorochloromethylmercaptophenyl- and 3-nitrophenyl-hydrazine.

The compounds (II) are prepared by reducing the corresponding phenyldiazonium chlorides with tin(II) chloride in hydrochloric acid solution, in the generally known manner.

Dicarboxylic acid anhydrides of the formula (III) which can be used are maleic anhydride, succinic anhydride, itaconic anhydride, citraconic anhydride, glutaric anhydride, 1,2-cyclopentanedicarboxylic acid anhydride, 1,2-cyclohexanedicarboxylic acid anhydride, Δ$^4$-cyclohexenedicarboxylic acid anhydride and phthalic anhydride. These compounds are generally known.

The active compounds which can be used according to the invention exhibit a powerful fungitoxic action and a bacteriotoxic action. They do not damage crop plants in the concentrations required for combating fungi and bacteria and have a low toxicity to warm-blooded animals. For these reasons, they are suitable for use as plant protection agents for combating fungi and bacteria. Fungitoxic agents in plant protection are employed for combating *Plasmodiophoromycetes, Oomycetes, Chytridiomycetes, Zygomycetes, Ascomycetes, Basidiomycetes* and *Deuteromycetes*.

The active compounds usable according to the invention can be employed against parasitic fungi and bacteria which attack above-ground parts of plants or attack the plants through the soil, and also against seed-borne pathogens. For example, they show, in particular, a good action against seed-borne mycoses caused by species of *Helminthosporium*, for example against stripe disease of barley.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polmeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellants, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions powders, pastes and granules. They may be used in the customary manner, for example by watering, spraying, atomizing, dusting, scattering, dry dressing, moist dressing, wet dressing, slurry dressing or encrusting.

In general, amounts of active compound of 10 mg to 10 g, preferably 100 mg to 3 g, are used for dressing, per kilogram of seed. In the case of treatment of soil, which can be carried out over the entire surface, in strips or in spots, active compound concentrations of 1 to 1,000 g of active compound per $m^3$ of soil, preferably 10 to 200 g per $m^3$, are generally employed at the locus of the required action.

The following examples illustrate preparation of the active compounds:

EXAMPLE 1

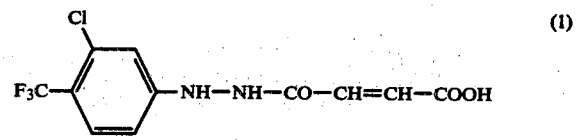

10.5 g (0.05 mol) of 3-chloro-4-trifluoromethylphenylhydrazine were dissolved in 50 ml of toluene. 4.9 g of maleic anhydride (0.05 mol) in the solid form were introduced into this solution at room temperature. This caused the temperature to rise by a few degrees, while the reaction product precipitated in the crystalline form. The mixture was then heated to about 50° C. for some time, after which it was allowed to cool and the product was filtered off. 10 g (65% of theory) of maleic acid mono-(3-chloro-4-trifluoromethyl-phenyl)-hydrazide of melting point 180°–182° C. were obtained.

3-Chloro-4-trifluoromethylphenylhydrazine, required as an intermediate, had a melting point of 42°–43° C. It was prepared by diazotizing of 3-chloro-4-trifluoromethylaniline and subsequent reduction of the corresponding phenyldiazonium chloride with tin(II) chloride.

EXAMPLE 2

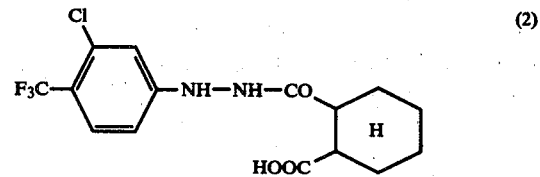

10.5 g (0.05 mol) of 3-chloro-4-trifluoromethylphenylhydrazine were dissolved in 70 ml of toluene and a solution of 7.7 g (0.05 mol) of hexahydrophthalic anhydride in 30 ml of toluene was added. No visible increase in temperature occurred. The mixture was stirred for 1 hour at 50° to 60° C. and was then cooled, 30 ml. of petroleum ether were added in order to precipitate the product, and the latter was filtered off. The melting point of hexahydrophthalic acid mono-(3-chloro-4-trifluoromethylphenyl)-hydrazide was 192°–193° C.

The following compounds of the general formula

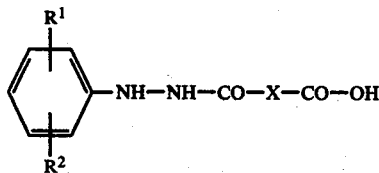

could be prepared in a similar manner:

Table 1

| Compound No. | R¹ | R² | X | Melting point (°C.) |
|---|---|---|---|---|
| 3 | H | H | CH=CH | 138-139 |
| 4 | 2-Cl | H | CH=CH | 157-158 |
| 5 | 3-Cl | H | CH=CH | 128-130 |
| 6 | 4-Cl | H | CH=CH | 160-161 |
| 7 | 3-NO₂ | H | CH=CH | 144-145 |
| 8 | 2-NO₂ | 4-NO₂ | CH=CH | 175-177 |
| 9 | 3-CF₃ | H | CH=CH | 120-122 |
| 10 | 4-CF₃ | 3-Cl | CH₂—CH₂ | 148-150 |
| 11 | 4-CF₃ | 3-Cl | C—CH₂ ‖ CH₂ | 135 |
| 12 | 4-CF₃ | 3-Cl | (CH₂)₃ | 173-174 |
| 13 | 4-CF₃ | 3-Cl | CH=C—CH₃ | 129-130 |
| 14 | 3-CF₃ | H | CH₂—CH₂ | 137-139 |
| 15 | 3-CF₃ | 4-CH₃ | CH=CH | 121-123 |
| 16 | 4-CF₃ | 3-Cl | (cyclohexyl) | 155-157 |
| 17 | 4-CF₃ | 3-Cl | (cyclobutyl) | 159 |
| 18 | 3-CF₃ | H | (cyclohexyl) | 151-153 |

Other compounds which can be similarly prepared include:

Table 2

| R¹ | R² | X |
|---|---|---|
| 4-CH₃ | H | (phenyl) |
| 4-OCH₃ | H | CH=CH |
| 4-SCH₃ | H | CH=CH |
| 3-OCF₃ | H | CH=CH | and the like.

The activity of the compounds of this invention is illustrated by the following example wherein the compounds according to the present invention are each identified by the number (given in brackets) from preparative examples hereinabove.

The known comparison compound is identified as follows:

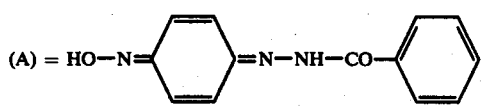

(A) = HO—N=⟨⟩=N—NH—CO—⟨⟩

EXAMPLE 3

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. Two batches of 50 grains of the pregerminated barley were subsequently sown 3 cm deep in Fruhstorfer standard soil and cultivated in a greenhouse at temperatures of 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentrations of the active compounds in the dressing, the amounts of dressing used and the number of diseased plants can be seen from the following table:

Table 3

Seed dressing test/stripe disease of barley

| Active compound | Active compound concentration in the dressing in % by weight | Amount of dressing used in g/kg of seed | Number of diseased plants in % of the total number of emerged plant |
|---|---|---|---|
| No dressing | — | — | 27.3 |
| (A) | 25 | 2 | 2.30 |
| (1) | 25 | 2 | 0.0 |
| (3) | 25 | 2 | 0.0 |
| (4) | 25 | 2 | 0.0 |
| (5) | 25 | 2 | 0.0 |
| (6) | 25 | 2 | 5.0 |
| (7) | 25 | 2 | 0.0 |
| (9) | 25 | 2 | 1.0 |
| (10) | 25 | 2 | 0.0 |
| (11) | 25 | 2 | 1.0 |
| (12) | 25 | 2 | 0.0 |
| (13) | 25 | 2 | 1.0 |
| (2) | 25 | 2 | 14.0 |
| (16) | 25 | 2 | 5.0 |
| (17) | 25 | 2 | 1.0 |
| (18) | 25 | 2 | 2.1 |

It will be appreciated that the instant specification and examples are set forth by way of illustration and not limitation, and that various modifications and changes may be made without departing from the spirit and scope of the present invention.

What we claim is:

1. A method of combating fungi which comprises applying to the fungi, or to a habitat thereof, a fungicidally effective amount of at least one dicarboxylic acid monoarylhydrazide, or a salt thereof, of the formula

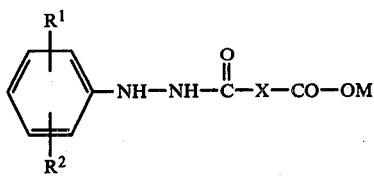

in which
- $R^1$ and $R^2$ each independently is hydrogen, halogen, $C_1$-$C_4$ alkyl, $C_1$-$C_4$ alkoxy, $C_1$-$C_4$ alkylmercapto, trihalogenomethyl, trihalogenomethoxy, trihalogenomethylmercapto or nitro,
- X is an alkylene, alkenylene, cycloalkylene, cycloalkenylene, cycloalkadienylene or phenylene radical, and
- M is hydrogen or one equivalent of an alkali or alkaline earth metal or ammonium.

2. The method according to claim 1, in which $R^1$ and $R^2$ each independently is hydrogen, chlorine, methyl, methoxy, methylmercapto, trifluoromethyl, trifluoromethoxy, trifluoromethylmercapto or nitro, and
- X is an alkylene or alkenylene radical with 2 to 4 carbon atoms, a cycloalkylene, cycloalkenylene or cycloalkadienylene radical with 4 to 7 carbon atoms or a phenylene radical.

3. The method according to claim 1, wherein such dicarboxylic acid mono-arylhydrazide is maleic acid mono(3-chloro-4-trifluoromethyl-phenyl)-hydrazide of the formula

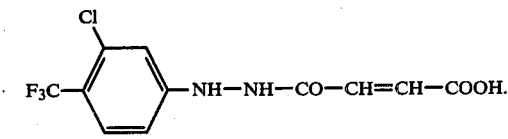

4. The method according to claim 1, wherein such dicarboxylic acid mono-arylhydrazide is maleic acid mono(3-chloro-phenyl)-hydrazide of the formula

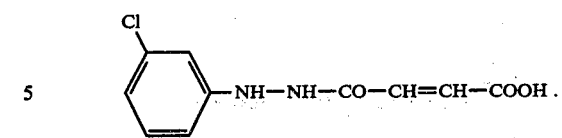

5. The method according to claim 1, wherein such dicarboxylic acid mono-arylhydrazide is maleic acid mono(3-trifluoromethyl-phenyl)-hydrazide of the formula

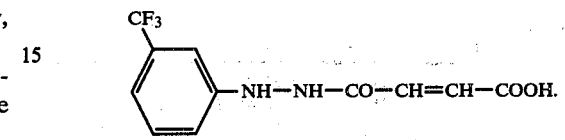

6. The method according to claim 1, wherein such dicarboxylic acid mono-arylhydrazide is maleic acid mono(4-choro-3-trifluoromethyl-phenyl)-hydrazide of the formula

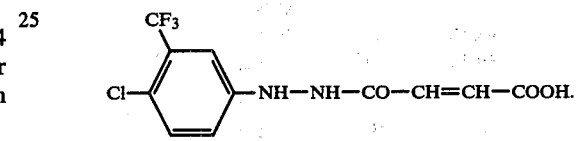

7. The method according to claim 1, wherein such dicarboxylic acid mono-arylhydrazide is 1,2-cyclohexene-4-dicarboxylic acid mono-(3-chloro-4-trifluoromethyl-phenyl)-hydrazide of the formula

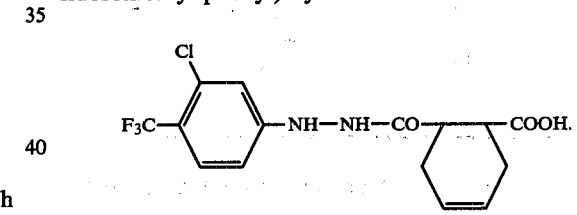

* * * * *